United States Patent
Jang et al.

(10) Patent No.: US 11,166,899 B2
(45) Date of Patent: Nov. 9, 2021

(54) **COMPOSITION FOR EXTERNAL APPLICATION CONTAINING A CERAMIDE, A DERIVATIVE THEREOF AND AN EXTRACT OF *HIBISCI CORTEX***

(71) Applicant: AMOREPACIFIC CORPORATION, Seoul (KR)

(72) Inventors: Dong Hyuk Jang, Yongin-si (KR); Sung Il Park, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 16/637,354

(22) PCT Filed: Aug. 6, 2018

(86) PCT No.: PCT/KR2018/008902
§ 371 (c)(1),
(2) Date: Feb. 7, 2020

(87) PCT Pub. No.: WO2019/031790
PCT Pub. Date: Feb. 14, 2019

(65) Prior Publication Data
US 2020/0179260 A1    Jun. 11, 2020

(30) Foreign Application Priority Data
Aug. 9, 2017 (KR) ................ 10-2017-0100966

(51) Int. Cl.
| | |
|---|---|
| *A61K 36/00* | (2006.01) |
| *A61K 8/68* | (2006.01) |
| *A61K 8/9789* | (2017.01) |
| *A61K 8/31* | (2006.01) |
| *A61K 8/34* | (2006.01) |
| *A61K 8/36* | (2006.01) |
| *A61K 8/63* | (2006.01) |
| *A61K 8/73* | (2006.01) |
| *A61K 8/92* | (2006.01) |
| *A61Q 19/00* | (2006.01) |
| *A61Q 19/08* | (2006.01) |

(52) U.S. Cl.
CPC ............... *A61K 8/68* (2013.01); *A61K 8/31* (2013.01); *A61K 8/34* (2013.01); *A61K 8/345* (2013.01); *A61K 8/361* (2013.01); *A61K 8/63* (2013.01); *A61K 8/735* (2013.01); *A61K 8/925* (2013.01); *A61K 8/9789* (2017.08); *A61Q 19/007* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 6,060,612 A | 5/2000 | Hong et al. | |
| 2011/0213031 A1* | 9/2011 | Tanaka ................ | A61K 8/68 514/549 |

FOREIGN PATENT DOCUMENTS

| | | |
|---|---|---|
| CN | 104523554 A | 4/2015 |
| CN | 10-2017-0112454 A | 10/2017 |
| JP | 2001-270816 A | 10/2001 |
| KR | 10-0181104 B1 | 5/1999 |
| KR | 10-0236304 B1 | 12/1999 |
| KR | 10-2010-0059302 A | 6/2010 |
| KR | 2010059302 A * | 6/2010 |
| KR | 2017038249 A * | 4/2017 |

OTHER PUBLICATIONS

Choi Sin Hye, "Mamonde conducts 'Mugunghwa Moisturizing Barrier Cream' sampling event", Sports Seoul, Jan. 7, 2016, p. 1-2 <URL: http://www.sportsseoul.com/news/read/341845> See p. 2.
International Search Report for PCT/KR2018/008902, dated Nov. 14, 2018.

* cited by examiner

Primary Examiner — Qiuwen Mi
(74) Attorney, Agent, or Firm — Sughrue Mion, PLLC

(57) ABSTRACT

The present disclosure relates to an external-use skin preparation composition containing a natural ceramide, a ceramide derivative, and a *Hibisci cortex* extract, and more specifically, the present disclosure relates to an external-use skin preparation composition containing these ingredients, thereby being effective for enhancing skin moisturizing ability, reducing skin wrinkles, and enhancing elasticity. In addition, the present disclosure relates to use of the composition, and a method for improving skin moisturization, reducing skin wrinkles, and/or improving skin elasticity by using the composition.

6 Claims, No Drawings

COMPOSITION FOR EXTERNAL APPLICATION CONTAINING A CERAMIDE, A DERIVATIVE THEREOF AND AN EXTRACT OF *HIBISCI CORTEX*

CROSS REFERENCE TO RELATED APPLICATIONS

This application is a National Stage of International Application No. PCT/KR2018/008902 filed Aug. 6, 2018, claiming priority based on Korean Patent Application No. 10-2017-0100966 filed Aug. 9, 2017.

TECHNICAL FIELD

The present disclosure relates to an external-use skin preparation composition containing a natural ceramide, a ceramide derivative, and a *Hibisci cortex* extract, and more particularly to an external-use skin preparation composition containing these ingredients, thereby being effective for enhancing skin moisturizing ability, reducing skin wrinkles, and enhancing elasticity. In addition, the present disclosure relates to use of the composition, and a method for improving skin moisturization, reducing skin wrinkles, and/or improving skin elasticity by using the composition.

BACKGROUND ART

The surface of human epidermis is protected by corneocytes, which are degenerated keratinocytes that have differentiated and grown from the stratum basal layer. The corneocytes function to maintain the smoothness and elasticity of the skin by binding to the double-chained lamellar structure of ceramides, which are abundantly present in the stratum corneum. A ceramide compound found in the human stratum corneum contains sphingosine or phytosphingosine in the structure.

However, skin aging reduces ceramide content in the stratum corneum with advancing age, leading to a decrease in the binding ability of corneocytes to the skin surface, and ultimately, the stratum corneum cannot serve as a protective barrier. As the ceramide content decreases, transepidermal water loss, exposure to the exterior irritation such as UV or chemicals, and peeling off of the corneocytes may occur, and thus the skin surface may be rough and damaged.

It has been reported that when the ceramide content in the stratum corneum decreases due to skin aging or damage to the stratum corneum by exterior irritation, an external supplementation of ceramides can recover the lamella structure, thereby recovering the skin to its normal state. In addition, the lamellar structure of the skin surface is not formed by ceramide alone, but is formed when other lipids present in the stratum corneum, for example, fatty acids or cholesterol coexist.

As such research results have been reported, studies have been conducted to find natural ceramides in animals, plants, and microorganisms for the purpose of the external supplementation of ceramides. As a result, various animals, plants, and microorganisms containing ceramides have been discovered.

However, the content of ceramides present in these animal, plants, and microorganisms is very low, and the extraction thereof requires a high production cost. In addition to the disadvantages, the natural ceramides have a low solubility in various organic solvents, and raw materials used in cosmetic and cleansing products, or the like, and thus only small amount of ceramides can be used in the manufacture of these products, failing to sufficiently provide the original effects.

PRIOR ART LITERATURES (Patent Literature 1) Korean Patent Registration No. 10-0236304 (published on Dec. 15, 1999)
(Patent Literature 2) Korean Patent Registration No. 10-0181104 (published on May 15, 1999)
(Patent Literature 3) Korean Unexamined Patent Publication No. 10-2010-0059302 (published on Jun. 4, 2010)

Technical Problem

In order to solve the above problems, the present inventors have made extensive efforts to find ingredients capable of exhibiting synergistic effects when used together with natural ceramide among various natural plant extracts, without suppressing the efficacy of the natural ceramide itself, and in particular, showing excellent effects even when applied to actual skin. Thus, by applying a *Hibisci cortex* extract together with a natural ceramide and a ceramide compound manufactured via synthesis, they have found that the recovery of the damaged skin, skin protection effect, skin moisturizing ability, and anti-aging effect of the skin are enhanced, thereby completing the present disclosure.

Accordingly, one object of the present disclosure is to provide an external-use skin preparation composition, which can exhibit effects of enhancing skin moisturizing ability, anti-aging of the skin, or the like, by containing a natural ceramide, a ceramide derivative, and a *Hibisci cortex* extract. Another object of the present disclosure is to provide the use of the composition in improving skin moisturizing ability, reducing skin wrinkles, and/or enhancing skin elasticity, and a method for improving skin moisturization, reducing skin wrinkles, and/or enhancing skin elasticity by using the composition.

Technical Solution

In order to achieve the objects above, the present disclosure provides an external-use skin preparation composition containing a natural ceramide, a ceramide derivative, and a *Hibisci cortex* extract, as an active ingredient, use of the composition, and a method for improving skin moisturization, reducing skin wrinkles, and/or enhancing skin elasticity by using the composition.

Advantageous Effects

The an external-use skin preparation composition of the present disclosure may not only recovers damaged skin, protects the skin from exterior irritation, and causes no irritation to the skin, but also shows effects of recovering and preventing the skin damaged by exterior environmental changes, and provides excellent effects in enhancing skin elasticity, preventing and improving skin aging, and enhancing skin moisturizing ability.

DETAILED DESCRIPTION OF THE EMBODIMENTS

The present disclosure relates to an external-use skin preparation composition containing a natural ceramide, a ceramide derivative, and a *Hibisci cortex* extract, as an active ingredient.

The natural ceramide contained in the composition of the present disclosure has a structure represented by the following Chemical Formulae 3 to 9, which contain sphingosine represented by chemical Formula 1 or phytosphingosine represented by Chemical Formula 2 in the structure.

[Chemical Formula 1]

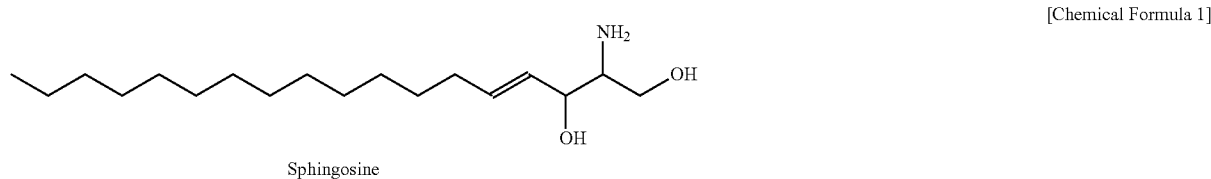

Sphingosine

[Chemical Formula 2]

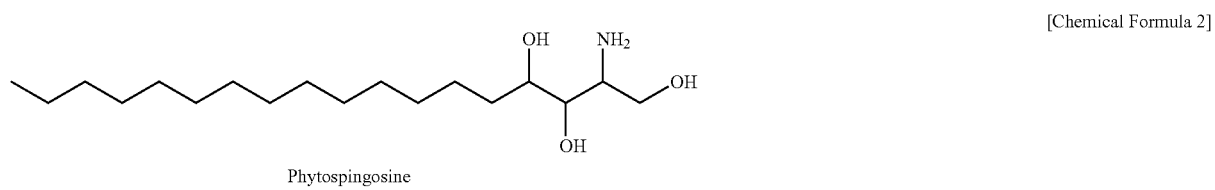

Phytospingosine

[Chemical Formula 3]

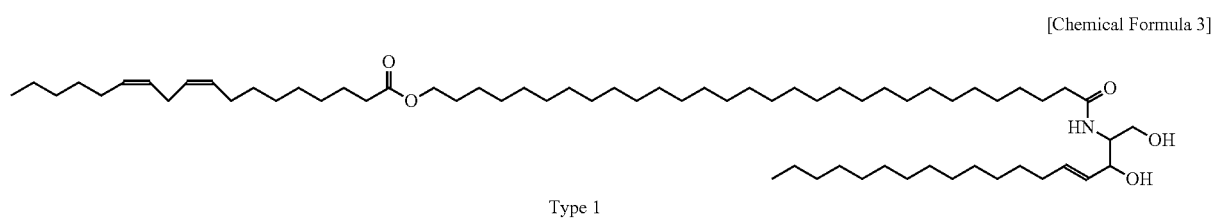

Type 1

[Chemical Formula 4]

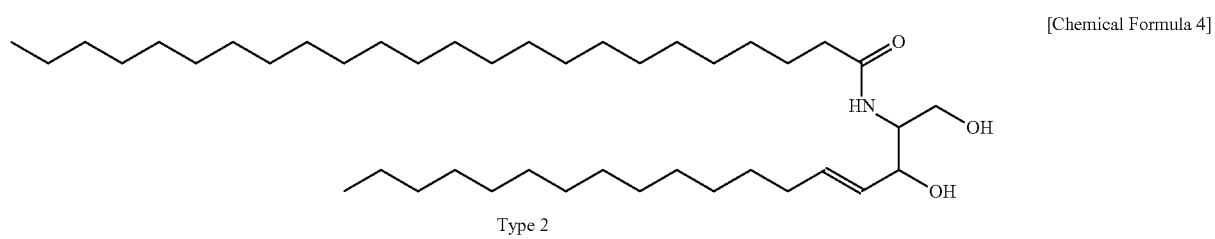

Type 2

[Chemical Formula 5]

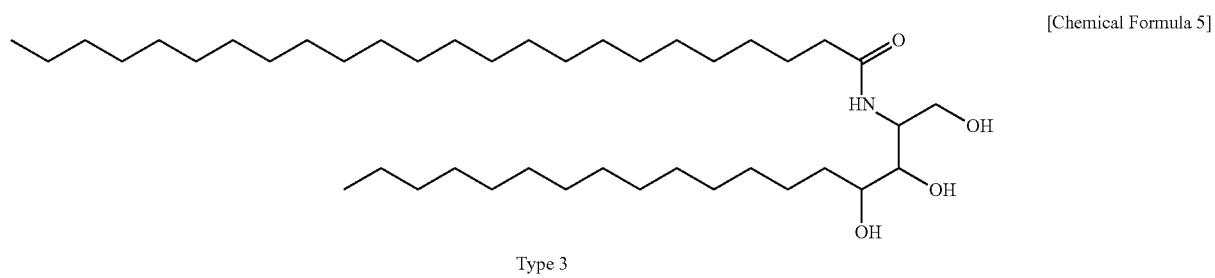

Type 3

[Chemical Formula 6]

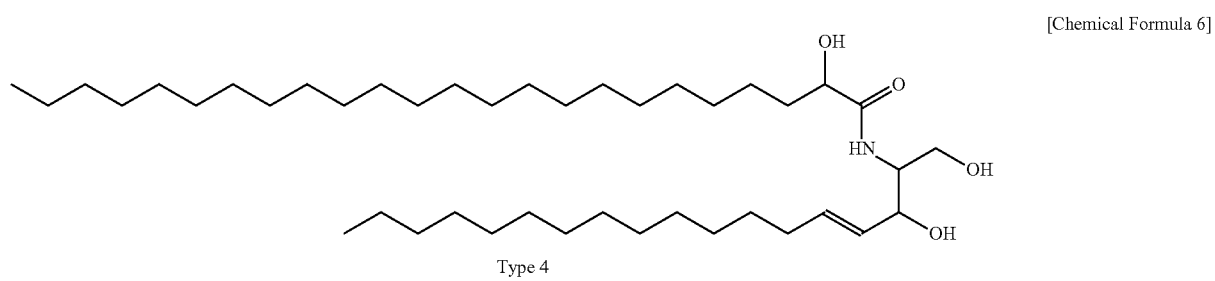

Type 4

-continued

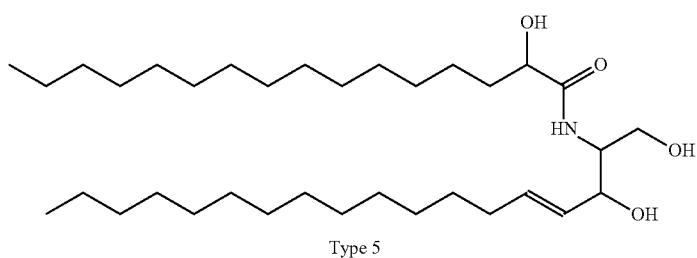
Type 5
[Chemical Formula 7]

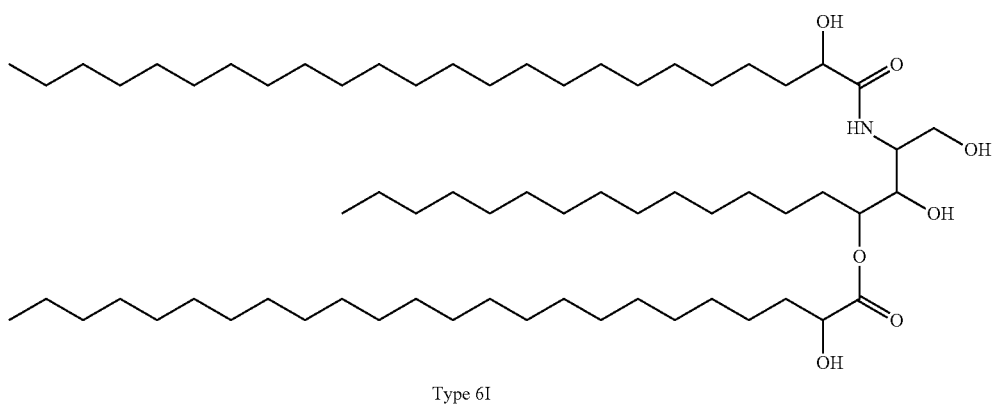
Type 6I
[Chemical Formula 8]

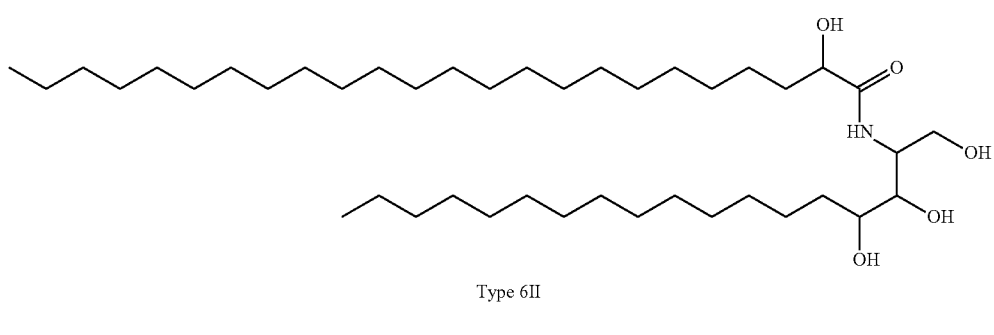
Type 6II
[Chemical Formula 9]

The natural ceramide used in the present disclosure may be extracted from plants, animals, microorganisms, or the like, and the origin thereof is not particularly limited. In the present disclosure, the natural ceramide may be directly extracted to be used, or a commercial product may be used.

The ceramide derivative used in the present disclosure is a ceramide having a chemical structure similar to that of the natural ceramide, and refers to a ceramide obtained by modifying or artificially synthesizing the natural ceramide. The Type of the ceramide derivative is not particularly limited as long as it can be applied to the skin, and preferably, it may be one or more selected from the group consisting of the compound of Chemical Formula 10 below (hereinafter, referred to as "P-104"), the compound of Chemical Formula 11 below (hereinafter, referred to as "P-102"), and a mixture thereof. More specifically, the ceramide derivative used in the present disclosure may be one or more selected from the group consisting of P-104 disclosed in Korean Patent Registration No. 10-0236304 (published on Dec. 15, 1999), P-102 disclosed in Korean Patent Registration No. 10-0181104 (published on May 15, 1999), and a mixture thereof.

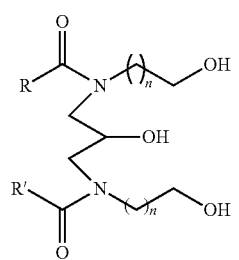
[Chemical Formula 10]

(wherein, n is 1 or 2, and R and R' are each independently a saturated or unsaturated $C_9$-$C_{21}$ aliphatic chain).

[Chemical Formula 11]

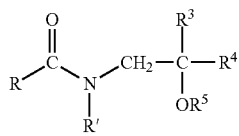

(wherein, R and R' are the same or different from each other, and are each independently a linear or branched, saturated or unsaturated $C_{10}$-$C_{32}$ alkyl group with or without a hydroxyl group, $R^3$ and $R^4$ are each independently hydrogen or a $C_1$-$C_4$ alkyl group or hydroxyalkyl group, and $R^5$ is -A or —$CH_2CH_2OA$, wherein A is any one of substituents of the following structures:

A;

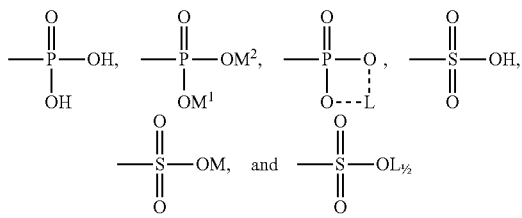

wherein, M, $M^1$, and $M^2$ are one selected from the group consisting of an alkali metal, lysine, arginine, histidine, triethanolamine, ammonia, polyquaternium-4, polyquaternium-6, polyquaternium-7, polyquaternium-10, polyquaternium-11, polyquaternium-16, lauryl dimethyl benzyl ammonium chloride, and stearyl dimethyl benzyl ammonium chloride, and L is an alkaline earth metal).

The *Hibisci cortex* used in the present disclosure is a dried bark from the roots and stems of *Hibiscus syriacus* L., which is a deciduous shrub in the Malvaceae family. The bark from the roots and stems are peeled off and dried in the sun during the spring. The taste is sweet and bitter, and it has neutral characteristics. It acts on the liver, spleen, large intestines, and small intestines. It clears heat, eliminates dampness, and detoxifies and kill parasites. In addition, it helps blood circulation and hemostasis. It is used to treat intestinal bleeding, dysentery, rectocele, leucorrhea, scabies, athlete's foot, haemorrhoids, or the like. When taking 3 to 9 g per day as a decoction medicine or using as an external medicine, it is washed with a boiled water or applied by soaking in wine.

The *Hibisci cortex* used in the present disclosure may be commercially available or prepared by a commonly-used preparation method.

In addition, the preparation method of the *Hibisci cortex* extract of the present disclosure is not particularly limited, and specifically, it may be prepared by the following method.

The *Hibisci cortex* extract used in the present disclosure may be obtained by extracting *Hibisci cortex* using water or an organic solvent. In one embodiment, the organic solvent may be one or more selected from the group consisting of ethanol, methanol, butanol, ether, ethyl acetate, and chloroform, or a mixed solvent of these organic solvents and water may be used. Specifically, the *Hibisci cortex* may be extracted using 80% ethanol.

The *Hibisci cortex* extract used in the present disclosure is known to activate the peroxisome proliferator-activated receptor (PPAR), more specifically PPAR-α, and helps to enhance skin barrier by inducing the differentiation of corneocyte through the regulation of gene expression of PPAR.

Further, the *Hibisci cortex* extract increases the expression of the filaggrin gene, a precursor protein of the natural moisturizing factor (NMF) responsible for skin moisturization, and increases the expression of the transglutaminase 1 gene (TGase1), which plays a critical role in the formation of the cornified envelope. In addition, the extract has the effect of increasing the expression of the hyaluronic acid synthase 2 (HAS2) gene, which is responsible for the synthesis of hyaluronic acid, an extracellular matrix component that performs the function of skin moisture retention, and thus helps to enhance skin moisturization.

Moreover, the *Hibisci cortex* extract has the effects of increasing the expression of the HMOX1 gene involved in detoxification, and regulating the expression of IL-β and TNFα, which are inflammatory factors, and thus exhibits a wound healing-promoting effect or anti-aging effect.

In the composition according to one aspect of the present disclosure, the natural ceramide is contained in an amount of 0.001 to 10% by weight, preferably 0.005 to 7% by weight, more preferably 0.01 to 5% by weight, based on the total weight of the composition.

In the composition according to one aspect of the present disclosure, the ceramide derivative is contained in an amount of 0.001 to 20% by weight, preferably 0.01 to 10% by weight, more preferably 0.1 to 5% by weight, based on the total weight of the composition.

In the composition according to one aspect of the present disclosure, the *Hibisci cortex* extract is contained in an amount of 0.001 to 20% by weight, preferably 0.01 to 10% by weight, more preferably 0.1 to 5% by weight, based on the total weight of the composition. If the content of the *Hibisci cortex* extract is less than 0.1% by weight, the effects of inducing skin epidermal differentiation, imparting skin moisturization, and anti-aging effect by the compound cannot be effectively obtained, and if the content exceeds 10% by weight, it is rather inefficient because the increase in the effect is not significant compared to the increase in the content.

In addition, in the composition according to one aspect of the present disclosure, the natural ceramide, the ceramide derivative, and the *Hibisci cortex* extract may mixed in a combination ratio of 1 to 300:1 to 500:1 to 500, preferably 1 to 100:1 to 300:1 to 300, more preferably 1 to 100:10 to 300:10 to 300, even more preferably 1 to 10:10 to 50:10 to 50, in terms of the weight ratio, but the combination ratio is not limited thereto.

Further, in the composition according to one aspect of the present disclosure, when the ceramide derivatives P-104 and P-102 are contained together, the combination ratio thereof is preferably 1 to 10:1 to 10, more preferably 5 to 10:5 to 10, and most preferably, 8:7, in terms of the weight ratio.

The composition according to the invention provides the effects of inducing skin epidermal differentiation; imparting skin moisturizer; promoting wound healing; and anti-aging such as skin wrinkle reduction or skin elasticity improvement.

In addition, the present disclosure provides the use of the external-use skin preparation composition according to the present disclosure for enhancing skin moisturizing ability, reducing skin wrinkles, and/or improving skin elasticity.

Further, the present disclosure provides a method for improving any one of moisturization, wrinkles, and elasticity of the skin by topically applying the composition according to the present disclosure to the skin of a subject.

The composition according to the present disclosure may be prepared in the form of a pharmaceutical composition containing a natural ceramide, a ceramide derivative, and a *Hibisci cortex* extract, in an effective amount, and may include one or more non-toxic and pharmaceutically or dermatologically acceptable carriers, excipients, adjuvants, and the like commonly used in the art.

In addition, the external-use skin preparation composition according to the invention may be formulated by a known method using a pharmaceutically or dermatologically acceptable carrier and/or excipient. For example, the external-use skin preparation composition may be formulated in the form of a solution, suspension, or emulsion in an oil or aqueous medium, or in the form of a dry powder, which is to be dissolved in sterile, pyrogen-free water before use.

Further, the external-use skin preparation composition according to the invention may be formulated by a known method using a cosmetically or dermatologically acceptable carrier and/or excipient. When formulating the external-use skin preparation composition according to the present disclosure in the form of cosmetics, the formulation may include softening cosmetic water, astringent cosmetic water, nourishing cosmetic water, eye cream, nourishing cream, massage cream, cleansing cream, cleansing foam, cleansing water, powder, essence, facial pack or the like, but the formulation is not particularly limited.

Hereinafter, the constitution and effect of the present disclosure will be described in more detail by way of Example and Test Examples. However, these Examples and Test Examples are given for illustrative purposes only to help understanding of the present disclosure, and the scope of the invention is not intended to be limited to or by these Examples and Test Examples.

MODE FOR CARRYING OUT THE INVENTION

Reference Example 1

Preparation of Natural Ceramide

Among the six kinds of natural ceramides represented by the above Chemical Formulae 3 to 9, the ceramide represented by the Chemical Formula 5 (Type 3), which is derived from bovine brain, was mainly used in cosmetics, and thus, the ceramide of Chemical Formula 5 was prepared as the natural ceramide and used in the following Test Examples.

Reference Example 2-1

Preparation of Ceramide Derivative 1,3-Bis(N-(2-Hydroxyethyl)-Palmitoylamino)-2-Hydroxypropane (P-104(a))

48.9 g of ethanolamine and 200 ml of ethanol were added to a 500 ml round-bottom flask equipped with a reflux condenser, and thoroughly mixed, and then, 12.9 g of 1,3-dichloro-2-hydroxypropane was added dropwise over 1 hour. After refluxing for 4 hours, the mixture was cooled to room temperature, and potassium hydroxide ethanolic solution was added thereto to filter the resulting solid. The filtrate was then distilled under reduced pressure to remove the solvent and unreacted ethanolamine, and then ethanol and chloroform were added to the residue to precipitate the crystals. It was filtered and then dried under reduced pressure to obtain 13.1 g of N,N'-bis(2-hydroxyethyl)-2-hydroxy-1,3-propanediamine.

In another 500 ml round-bottom flask, 4.0 g of magnesium oxide was added to 80 g of water, and mixed by stirring. Subsequently, 8.9 g of N,N'-bis(2-hydroxyethyl)-2-hydroxy-1,3-propanediamine prepared above was added to the mixture, and then 250 ml of 1,4-dioxane was added. Then, 26.8 g of palmitoyl chloride was added dropwise over 1 hour, while violently stirring the mixture at room temperature. After stirring for another 2 hours, the mixture was filtered, and the solid on the filter was washed with 200 ml of chloroform. After the filtrate and the washing solution were combined, the water layer was separated and discarded, the organic layer was cooled, and the resulting solid was filtered. The solid was then dried and recrystallized in acetone to yield 24.3 g of 1,3-bis(N-(2-hydroxyethyl)-palmitoylamino)-2-hydroxypropane (P-104(a)) as a white solid.

Reference Example 2-2

Preparation of Ceramide Derivative 1,3-Bis(N-(2-Hydroxyethyl)-Lauroylamino)-2-Hydroxypropane (P-104(b))

In a 500 ml round-bottom flask, 4.0 g of magnesium oxide was added to 80 g of water, and mixed by stirring. Subsequently, 8.9 g of N,N'-bis(2-hydroxyethyl)-2-hydroxy-1,3-propanediamine prepared in Reference Example 2-1 was added to the mixture, and then 250 ml of 1,4-dioxane was added. Then, 21.3 g of lauroyl chloride was added dropwise over 1 hour, while violently stirring the mixture at room temperature. After stirring for another 2 hours, the mixture was filtered, and the solid on the filter was washed with 200 ml of chloroform. After the filtrate and the washing solution were combined, the water layer was separated and discarded, the organic layer was cooled, and the resulting solid was filtered. The solid was then dried and recrystallized in acetone to yield 19.5 g of 1,3-bis(N-(2-hydroxyethyl)-lauroylamino)-2-hydroxypro pane (P-104(b)) as a white solid.

Reference Example 2-3

Preparation of Ceramide Derivative 1,3-Bis(N-(2-Hydroxyethyl)-Oleoylamino)-2-Hydroxypropane (P-104(c))

In a 500 ml round-bottom flask, 4.0 g of magnesium oxide was added to 80 g of water, and mixed by stirring. Subsequently, 8.9 g of N,N'-bis(2-hydroxyethyl)-2-hydroxy-1,3-propanediamine prepared in Reference Example 2-1 above was added to the mixture, and then 250 ml of 1,4-dioxane was added. Then, 29.3 g of oleoyl chloride was added dropwise over 1 hour while violently stirring the mixture at room temperature. After stirring for another 2 hours, the mixture was filtered, and the solid on the filter was washed with 200 ml of chloroform. After the filtrate and the washing solution were combined, the water layer was separated and discarded, the organic layer was cooled, and the resulting solid was filtered. The solid was then dried and recrystallized in acetone to yield 27.2 g of 1,3-bis(N-(2-hydroxyethyl)-oleoylamino)-2-hydroxypropane (P-104(c)) as a white solid.

Reference Example 2-4

Preparation of Ceramide Derivative

N,N'-Bis(2-Hydroxyethyl)-N-Palmitoyl-N'-1,3-Diamino-2-Hydroxypropane (P-104(d))

59.0 g of 3-amino-1-propanol and 200 ml of ethanol were added to a 500 ml round-bottom flask equipped with a reflux condenser, and thoroughly mixed, and then, 9.3 g of epichlorohydrin was added dropwise over 1 hour. After refluxing for 4 hours, the mixture was cooled to room temperature, and potassium hydroxide ethanolic solution was added thereto to filter the resulting solid. The filtrate was then distilled under reduced pressure to remove the solvent and unreacted 3-amino-1-propanol, and ethanol and chloroform were added to the residue to precipitate the crystals. It was filtered and dried under reduced pressure to obtain 18.2 g of N,N'-bis(3-hydroxypropyl)-2-hydroxy-1,3-propanediamine.

In another 500 ml round-bottom flask, 4.0 g of magnesium oxide was added to 80 g of water, and mixed by stirring. Subsequently, 10.4 g of N,N'-bis(3-hydroxypropyl)-2-hydroxy-1,3-propanediamine prepared above was added to the mixture, and then 250 ml of 1,4-dioxane was added. Then, 13.4 g of palmitoyl chloride was added dropwise over 1 hour while violently stirring the mixture at room temperature. After stirring for another 2 hours at 10° C., 14.7 g of oleoyl chloride was added dropwise over 1 hour. After stirring for another 2 hours, the mixture was filtered, and the solid on the filter was washed with 200 ml of chloroform. After the filtrate and the washing solution were combined, the water layer was separated and discarded, the organic layer was cooled, and the resulting solid was filtered. The solid was then dried and recrystallized in acetone to yield 26.5 g of N,N'-bis(2-hydroxyethyl)-N-palmitoyl-N'-1,3-diamino-2-hydroxypropane (P-104(d)) as a white solid.

Reference Example 3-1

Preparation of Ceramide Derivative N-(2-Hydroxypropane)-N-Hexadecylamine (P-102(a))

In a 1 L round-bottom flask, 48.2 g of hexadecylamine was dissolved in 700 ml of ethanol. Subsequently, 18.9 g of 1-chloro-2-propanol was slowly added thereto at 40° C. After stirring for another 3 hours at the same temperature, a potassium hydroxide/ethanol solution was added, and the resulting solid was filtered. The filtrate was then concentrated under reduced pressure and recrystallized in ethanol to yield 36 g of N-(2-hydroxypropane)-N-hexadecylamine (yield: 60%; P-102(a)).

Reference Example 3-2

Preparation of Ceramide Derivative N-(2-Methyl-2-Hydroxypropane)-N-Hexadecylamine (P-102(b))

22.6 g of 1-chloride-2-methyl-2-propanol was used, instead of 1-chloro-2-propanol in Reference Example 3-1, which was then treated in the same manner as in Reference Example 3-1 to obtain 48.3 g of the title compound as a white powder (yield: 77%, P-102(b)).

Reference Example 3-3

Preparation of Ceramide Derivative N-(2-Ethoxy-2-Hydroxyethane)-N-Hexadecylamine (P-102(c))

23.2 g of 1-chloride-2-ethoxy-2-ethanol was used, instead of 1-chloro-2-propanol in Reference Example 3-1, which was then treated in the same manner as in Reference Example 3-1 to obtain 45.6 g of the title compound as a white powder (yield: 69%, P-102(c)).

Reference Example 3-4

Preparation of Ceramide Derivative N-(2-Hydroxypropane)-N-Oleylamine (P-102(d))

53.5 g of oleylamine was used, instead of hexadecylamine in Reference Example 3-1, which was then treated in the same manner as in Reference Example 3-1 to obtain 35.2 g of the title compound as a white powder (yield: 78%, P-102(d)).

Reference Example 3-5

Preparation of Ceramide Derivative N-(2-Methyl-2-Hydroxypropane)-N-Oleylamine (P-102(e))

53.5 g of oleylamine was used, instead of hexadecylamine in Reference Example 3-2, which was then treated in the same manner as in Reference Example 3-2 to obtain 35.2 g of the title compound as a white powder (yield: 78%, P-102(e)).

Reference Example 3-6

Preparation of Ceramide Derivative N-Hexadecyl-N-(2-Hydroxypropane)Hexadecanamide (P-102(f))

In a 250 ml flask equipped with a reflux condenser, 14.3 g of methyl palmitate was dissolved in 16 g of N-(2-hydroxypropane)-N-hexadecylamine prepared in Reference Example 3-1. Then, 2.6 g of sodium carbonate was added thereto, and the mixture was stirred violently at 120° C. for 3 hours. After the reaction was completed, the mixture was cooled to room temperature, and added with 100 ml of chloroform to dissolve the mixture. The insoluble matters were removed, and the solvent was distilled under reduced pressure. The resulting solid was recrystallized in hexane to obtain 21.6 g of N-hexadecyl-N-(2-hydroxypropane)hexadecanamide as a white solid (yield: 80%; P-102(f)).

Reference Example 3-7

Preparation of Ceramide Derivative N-Hexadecyl-N-(2-Methyl-2-Hydroxypropane)Hexadecanamide (P-102(g))

15.7 g of N-(2-methyl-2-hydroxypropane)-N-hexadecylamine prepared in Reference Example 3-2 and 14.9 g of methyl palmitate were treated in the same manner as in Reference Example 3-6 to obtain 24.6 g of N-hexadecyl-N-(2-methyl-2-hydroxypropane)hexadecanamide as a white solid (yield: 87%; P-102(g)).

Reference Example 3-8

Preparation of Ceramide Derivative N-Hexadecyl-N-(2-Ethoxy-2-Hydroxyethane)Hexadecanamide (P-102(h))

16.5 g of N-(2-ethoxy-2-hydroxyethane)-N-hexadecylamine prepared in Reference Example 3-3 and 14.9 g of methyl palmitate were treated in the same manner as in Reference Example 3-6 to obtain 24.2 g of N-hexadecyl-N-(2-ethoxy-2-hydroxyethane)hexadecanamide as a white solid (yield: 83%; P-102(h)).

Reference Example 3-9

Preparation of Ceramide Derivative N-Oleyl-N-(2-Hydroxypropane)Hexadecanamide (P-102(i))

16.3 g of N-(2-hydroxypropane)-N-oleylamine prepared in Reference Example 3-4 and 14.9 g of methyl palmitate were treated in the same manner as in Reference Example 3-6 to obtain 21.6 g of N-oleyl-N-(2-hydroxypropane)hexadecanamide as a white solid (yield: 78%; P-102 (i)).

Reference Example 3-10

Preparation of Ceramide Derivative N-Oleyl-N-(2-Methyl-2-Hydroxypropane)Hexadecanamide (P-102(j))

17 g of N-(2-methyl-2-hydroxypropane)-N-oleylamine prepared in Reference Example 3-5 and 14.9 g of methyl palmitate were treated in the same manner as in Reference Example 3-6 to obtain 21 g of N-oleyl-N-(2-methyl-2-hydroxypropane)hexadecanamide as a white solid (yield: 71%; P-102 (j)).

Reference Example 3-11

Preparation of Ceramide Derivative (N-Hexadecyl-N-Palmitoyl)-1-Aminopropane-2-Sodium Phosphate (P-102(k))

5.38 g of N-hexadecyl-N-(2-hydroxypropane)hexadecanamide prepared in Reference Example 3-6 and 1.15 g of phosphoric acid were added to 100 ml of dioxane, and the mixture was stirred at room temperature for 1 hour. Then 2.0 g of phosphorus pentoxide was added thereto and heated to reflux for 5 hours. After the reaction was completed, the mixture was cooled to room temperature and 3.8 ml of 40% aqueous sodium hydroxide solution was added thereto. Then, the reaction mixture was distilled under reduced pressure to remove the solvent, and subsequently, ethanol was added to remove the resulting precipitates. The residue was distilled under reduced pressure and subjected to column chromatography to obtain 4.1 g of (N-hexadecyl-N-palmitoyl)-1-aminopropane-2-sodium phosphate (yield: 66%; P-102(k)).

Reference Example 3-12

Preparation of Ceramide Derivative (N-Hexadecyl-N-Palmitoyl)-1-Amino-2-Methylpropane-2-Sodium Phosphate (P-102(l))

5.7 g of N-hexadecyl-N-(2-methyl-2-hydroxypropane)hexadecanamide prepared in Reference Example 3-7 was used, instead of N-hexadecyl-N-(2-hydroxypropane)hexadecanamide in Reference Example 3-11, which was then phosphorylated in the same manner as in Reference Example 3-11 to obtain the title compound (4.3 g, 64% yield; P-102(l)).

Reference Example 3-13

Preparation of Ceramide Derivative (N-Hexadecyl-N-Palmitoyl)-1-Amino-2-Ethoxyethane-2-Sodium Phosphate (P-102(m))

5.8 g of N-hexadecyl-N-(2-ethoxy-2-hydroxyethane)hexadecanamide prepared in Reference Example 3-8 was used, instead of N-hexadecyl-N-(2-hydroxypropane)hexadecanamide in Reference Example 3-11, which was then phosphorylated in the same manner as in Reference Example 3-11 to obtain the title compound (4.4 g, yield 64%; P-102(m)).

Reference Example 3-14

Preparation of Ceramide Derivative (N-Oleyl-N-Palmitoyl)-1-Aminopropane-2-Sodium Sulfate 5.8 g of N-oleyl-N-(2-hydroxypropane)hexadecanamide prepared in Reference Example 3-9 was added to 100 ml of dioxane and stirred, and 1.3 g of chlorosulfonic acid was slowly added dropwise at 10 to 15° C. After the dropwise addition was completed, the mixture was stirred at room temperature for 2 hours. After the reaction was completed, 3.0 ml of 40% aqueous sodium hydroxide solution was added to the mixture. Then, the reaction mixture was distilled under reduced pressure to remove the solvent, and subsequently, ethanol was added to remove the resulting precipitates. The residue was distilled under reduced pressure and subjected to column chromatography to obtain 4.9 g of (N-oleyl-N-palmitoyl)-1-aminopropane-2-sodium sulfate (yield: 72%; P-102(n)).

Reference Example 3-15

Preparation of Ceramide Derivative (N-Oleyl-N-Palmitoyl)-1-Amino-2-Methylpropane-2-Sodium Sulfate (P-102(o))

5.9 g of N-oleyl-N-(2-methyl-2-hydroxypropane)hexadecanamide prepared in Reference Example 3-10 was reacted with 1.3 g of chlorosulfonic acid, instead of N-oleyl-N-(2-hydroxypropane)hexadecanamide in Reference Example 3-14, which was then sulfated in the same manner as in Reference Example 3-14 to obtain the title compound (5.1 g, 73% yield; P-102(o)).

Reference Example 4

Preparation of *Hibisci cortex* Extract

A total of 1 kg of *Hibisci cortex*, which was finely cut and dried in the shade, was reflux extracted three times for 24 hours each with an aqueous 80% ethanol solution, which was then macerated and filtered through Whatman filter paper #5. The filtered extract was concentrated under reduced pressure at 45° C. or below and freeze-dried at −60° C. for 3 days.

The *Hibisci cortex* extract was prepared by dispersing/dissolving the extract using ethanol such that the concentrate prepared under reduced pressure was contained in an amount of 5% by weight based on the total weight of the *Hibisci cortex* extract.

Test Example 1

Confirmation of PPARα Activation of Single Ceramide Derivatives

HaCaT, which is a human keratinocyte cell line, was subcultured in DMEM medium containing 10% fetal bovine serum, which is a phenol red-free medium, in order to eliminate the effect caused by the phenol red's estrogen. The following plasmids were used: a plasmid having PPARα, PPARβ/δ and PPARγ genes downstream of a universal promoter which is expressed in general culture conditions; a plasmid having a PPARs response element ("PPRE") as a promoter, which is activated by binding with ligand-bound PPARs, and a firefly luciferase gene serving as a reporter downstream of the promoter; and a reference plasmid having a β-galactosidase gene bound to a universal promoter.

HaCaT cells were seeded into a 24-well plate at a density of $5×10^4$ cells/well, cultured for 24 hours, and then transiently transfected with the plasmid genes. After 24 hours of culture, the cells were washed with phosphate buffered saline (PBS), and then treated with the compounds prepared in Reference Examples 2-1 to 2-4, and Reference Examples 3-11 to 3-15 at a concentration of 10 ppm. As a positive control group, the cells were treated with a previously-known PPARs ligand (PPARα ligand Wy-14643) at a concentration of 10 μM. As a negative control group, a group treated with DMSO used to dissolve the samples was used. After 24 hours of culture, the cells were washed with PBS, harvested, and measured for luciferase activity. The measurement results are shown in Table 1 below.

TABLE 1

| | Relative to Control Group (%) |
|---|---|
| Negative Control Group | 100 |
| Positive control Group (Wy-14643, 10 μM) | 291 |
| Reference Example 2-1 (10 ppm) | 263 |
| Reference Example 2-2 (10 ppm) | 270 |
| Reference Example 2-3 (10 ppm) | 255 |
| Reference Example 2-4 (10 ppm) | 260 |
| Reference Example 3-11 (10 ppm) | 272 |
| Reference Example 3-12 (10 ppm) | 270 |
| Reference Example 3-13 (10 ppm) | 259 |
| Reference Example 3-14 (10 ppm) | 278 |
| Reference Example 3-15 (10 ppm) | 269 |

Results obtained by transfecting the HaCaT cell line with the PPRE promoter reporter plasmid and the PPARα expression plasmid, followed by treating the transfected cells with drugs, and measuring the luciferase activity of the cells As shown in the above results, it can be seen that the ceramide derivatives generally induced the PPARα activity at a similar level.

Therefore, in the following Test Examples, those showing intermediate activity among the ceramide derivatives were selected and used, specifically, as a representative example of P-104, the compound of Reference Example 2-1 was used, and as a representative example of P-102, the compound of Reference Example 3-11 was used.

Reference Example 5

Preparation of Examples 1 to 4 and Comparative Examples 1 to 9

The natural ceramide of Reference Example 1, the ceramide derivative (P-104) of Reference Example 2-1 or the ceramide derivative (P-102) of Reference Example 3-11, and the *Hibisci cortex* extract of Reference Example 4 were mixed in various combination ratios as shown in Table 2 below to prepare Examples 1-4 and Comparative Examples 1-9.

TABLE 2

(Unit: Wt %)

| | Comparative Examples | | | | | | | | | Examples | | | |
|---|---|---|---|---|---|---|---|---|---|---|---|---|---|
| Component | 1 | 2 | 3 | 4 | 5 | 6 | 7 | 8 | 9 | 1 | 2 | 3 | 4 |
| Ceramide P-102 | 1.9 | 0 | 0 | 1.4 | 1.4 | 0 | 1.6 | 1.6 | 1.81 | 1.4 | 1.1 | 1 | 1.33 |
| Ceramide P-104 | 2.1 | 0 | 0 | 1.6 | 1.6 | 0 | 1.83 | 1.83 | 2.06 | 1.6 | 1.25 | 1 | 1.53 |
| Natural ceramide | 0 | 4 | 0 | 1 | 0 | 3 | 0.57 | 0 | 0.13 | 0.5 | 0.08 | 1 | 0.57 |
| Hibisci Cortex extract | 0 | 0 | 4 | 0 | 1 | 1 | 0 | 0.57 | 0 | 0.5 | 1.57 | 1 | 0.57 |

Test Example 2

Confirmation of PPARα Activation of Natural Ceramide, Ceramide Derivatives, and *Hibisci cortex* Extract The effect of the combination of the natural ceramide, the ceramide derivatives (P-102 and P-104), and *Hibisci cortex* extract on PPARα activation was confirmed in the same manner as in Test Example 1, except that the cells were treated with Comparative Examples 1 to 9 and Examples 1 to 4 each at a concentration of 4 ppm, and as a negative control group, a group treated with DMSO used to dissolve the samples was used.

The measurement results of luciferase activity are shown in Table 3 below.

TABLE 3

| | Amount of PPARα Expression (relative to control %) |
|---|---|
| Control | 100 |
| Comparative Example 1 | 139 |
| Comparative Example 2 | 128 |
| Comparative Example 3 | 120 |
| Comparative Example 4 | 159 |
| Comparative Example 5 | 151 |
| Comparative Example 6 | 132 |
| Comparative Example 7 | 162 |
| Comparative Example 8 | 160 |
| Comparative Example 9 | 173 |
| Example 1 | 285 |
| Example 2 | 297 |
| Example 3 | 236 |
| Example 4 | 271 |

As shown in Table 3, the expression amount of PPARα was increased when a combination of two components was used, compared to the expression amount obtained when the natural ceramide, the ceramide derivatives, and the *Hibisci cortex* extract were used alone. In case of Examples 1 to 4, in which all of three components were combined, it can be seen that the expression amount of PPARα was significantly increased due to the synergistic effect according to the combination of the components.

Reference Example 6

Preparation of Cosmetic Compositions Containing Natural Ceramide, Ceramide Derivatives, and *Hibisci cortex* Extract Cosmetic compositions containing the natural ceramide, the ceramide derivatives, and the *Hibisci cortex* extract were prepared as described in Table 4 below.

TABLE 4

|  | Components | Comparative Formulation Examples | | | | | | | | | | Formulation Examples | | | |
|---|---|---|---|---|---|---|---|---|---|---|---|---|---|---|---|
|  |  | 1 | 2 | 3 | 4 | 5 | 6 | 7 | 8 | 9 | 10 | 1 | 2 | 3 | 4 |
| Oil-phase | Ceramide P-102 | 0 | 1.9 | 0 | 0 | 1.4 | 1.4 | 0 | 1.6 | 1.6 | 1.81 | 1.4 | 1.1 | 1 | 1.33 |
|  | Ceramide P-104 | 0 | 2.1 | 0 | 0 | 1.6 | 1.6 | 0 | 1.83 | 1.83 | 2.06 | 1.6 | 1.25 | 1 | 1.53 |
|  | Natural Ceramide | 0 | 0 | 4 | 0 | 1 | 0 | 3 | 0.57 | 0 | 0.13 | 0.5 | 0.08 | 1 | 0.57 |
|  | Cholesterol | 1 | 1 | 1 | 1 | 1 | 1 | 1 | 1 | 1 | 1 | 1 | 1 | 1 | 1 |
|  | Stearic acid | 3 | 3 | 3 | 3 | 3 | 3 | 3 | 3 | 3 | 3 | 3 | 3 | 3 | 3 |
|  | Cetearyl Alcohol | 2 | 2 | 2 | 2 | 2 | 2 | 2 | 2 | 2 | 2 | 2 | 2 | 2 | 2 |
|  | Behenyl alcohol | 2 | 2 | 2 | 2 | 2 | 2 | 2 | 2 | 2 | 2 | 2 | 2 | 2 | 2 |
|  | Cetylethyl hexanoate | 10 | 10 | 10 | 10 | 10 | 10 | 10 | 10 | 10 | 10 | 10 | 10 | 10 | 10 |
| Aqueous-Phase | Butylene Glycol | 10 | 10 | 10 | 10 | 10 | 10 | 10 | 10 | 10 | 10 | 10 | 10 | 10 | 10 |
|  | Glycerin | 5 | 5 | 5 | 5 | 5 | 5 | 5 | 5 | 5 | 5 | 5 | 5 | 5 | 5 |
|  | Caprylyl Glycol | 0.1 | 0.1 | 0.1 | 0.1 | 0.1 | 0.1 | 0.1 | 0.1 | 0.1 | 0.1 | 0.1 | 0.1 | 0.1 | 0.1 |
|  | Tromethamine | 0.3 | 0.3 | 0.3 | 0.3 | 0.3 | 0.3 | 0.3 | 0.3 | 0.3 | 0.3 | 0.3 | 0.3 | 0.3 | 0.3 |
|  | Hibisci Cortex extract | 0 | 0 | 0 | 4 | 0 | 1 | 1 | 0 | 0.57 | 0 | 0.5 | 1.57 | 1 | 0.57 |
|  | Water | To 100 | To 100 | To 100 | To 100 | To 100 | To 100 | To 100 | To 100 | To 100 | To 100 | To 100 | To 100 | To 100 | To 100 |

Test Example 3

Sensory Evaluation—Wrinkle Reduction and Elasticity Improvement Effects

One hundred and forty 25- to 35-year-old women who were suffering from sagging skin were divided into 14 groups with 10 in each group, and they were asked to use each composition of Comparative Formulation Example 1 to and Formulation Examples 1 to 4 for four weeks in the same manner as using ordinary cosmetic products. After using the compositions for 1 week, a questionnaire was conducted every other week according to the following evaluation criteria to evaluate the degree of skin lifting effect including wrinkle reduction and elasticity improvement. The results are shown in Table 5 below.

TABLE 5

| Test Material | Duration | | | |
|---|---|---|---|---|
|  | $1^{st}$ week | $2^{nd}$ week | $3^{rd}$ week | $4^{th}$ week |
| Comparative Formulation Example 1 | ± | ± | ± | + |
| Comparative Formulation Example 2 | + | + | + | ++ |
| Comparative Formulation Example 3 | + | + | + | + |
| Comparative Formulation Example 4 | + | + | + | + |

TABLE 5-continued

| Test Material | Duration | | | |
|---|---|---|---|---|
|  | $1^{st}$ week | $2^{nd}$ week | $3^{rd}$ week | $4^{th}$ week |
| Comparative Formulation Example 5 | + | + | ++ | ++ |
| Comparative Formulation Example 6 | + | + | ++ | ++ |
| Comparative Formulation Example 7 | + | + | + | ++ |
| Comparative Formulation Example 8 | + | + | ++ | ++ |
| Comparative Formulation Example 9 | + | + | ++ | ++ |
| Comparative Formulation Example 10 | + | ++ | ++ | ++ |

TABLE 5-continued

| Test Material | 1st week | 2nd week | 3rd week | 4th week |
|---|---|---|---|---|
| Formulation Example 1 | ++ | ++ | +++ | +++ |
| Formulation Example 2 | ++ | ++ | +++ | +++ |
| Formulation Example 3 | ++ | ++ | ++ | +++ |
| Formulation Example 4 | ++ | ++ | +++ | +++ |

+++: Show a very good improvement effect.
++: Show a considerable improvement effect.
+: Show a slight improvement effect.
±: No improvement effect, but not worsened.
−: No improvement effect, and rather worsened.

As shown in Table 5, it can be seen that Formulation Examples 1 to 4 according to the present disclosure show a significantly higher skin lifting effect including skin wrinkle reduction and elasticity improvement, compared to Comparative Formulation Examples 2 to 10, which contain one or two of the natural ceramide, the ceramide derivatives, and the *Hibisci cortex* extract, and that the lifting effect of Formulation Examples 1 to 4 was achieved in a shorter time compared to Comparative Formulation Examples 1 to 10.

Test Examples 4

Sensory Evaluation—Feeling of Use and Moisturizing Ability

The feeling of use and moisturizing ability of Comparative Formulation Examples 1 to 10 and Formulation Examples 1 to 4 were evaluated. The evaluation was carried out as a sensory evaluation by 10 evaluators professionally trained on the evaluation of feeling of use of cosmetics. The evaluation was carried out for applicability, stickiness, and moisturizing feeling on a scale of 1 to 5. The evaluation of applicability was carried out on the following criteria: a score of 5 for good applicability and a score of 1 for bad applicability. The evaluation of stickiness was carried out on the following criteria: a score of 1 for low stickiness and a score of 5 for high stickiness. The evaluation of moisturizing feeling was carried out on the following criteria: a score of 5 for high moisturizing feeling and a score of 1 for low moisturizing feeling. After the evaluation of each product, the scores of each evaluation item were calculated as an average value of 10 people, and the results are shown in Table 6 below.

TABLE 6

| | Applicability | Stickiness | Moisturizing Feeling |
|---|---|---|---|
| Comparative Formulation Example 1 | 4.1 | 1.5 | 1.8 |
| Comparative Formulation Example 2 | 3.6 | 2.3 | 2.9 |
| Comparative Formulation Example 3 | 3.5 | 2.4 | 2.7 |
| Comparative Formulation Example 4 | 3.8 | 1.8 | 3.1 |
| Comparative Formulation Example 5 | 4.1 | 1.9 | 3.5 |
| Comparative Formulation Example 6 | 4.2 | 1.8 | 3.6 |
| Comparative Formulation Example 7 | 4.1 | 1.9 | 3.2 |
| Comparative Formulation Example 8 | 4.0 | 2.1 | 3.8 |
| Comparative Formulation Example 9 | 4.2 | 2.0 | 3.7 |
| Comparative Formulation Example 10 | 4.2 | 2.2 | 3.9 |
| Formulation Example 1 | 4.7 | 1.2 | 4.8 |
| Formulation Example 2 | 4.8 | 1.2 | 4.9 |
| Formulation Example 3 | 4.4 | 1.3 | 4.3 |
| Formulation Example 4 | 4.5 | 1.2 | 4.5 |

As shown in Table 6, Formulation Examples 1 to 4 according to the present disclosure exhibited a significantly higher effect on moisturizing ability, while exhibiting a similar or higher degree of feeling of use, such as applicability and stickiness, compared to Comparative Formulation Examples 2 to 10, which contain one or two of the natural ceramide, the ceramide derivatives, and the *Hibisci cortex* extract.

Preparation Example 1

Nourishing Cosmetic Water

A nourishing cosmetic water was prepared by a conventional manner according to the composition shown in Table 7 below.

TABLE 7

| Components | Content(wt %) |
|---|---|
| Purified Water | Residual amount |
| Glycerin | 8.0 |
| Butylene glycol | 4.0 |
| Hyaluronic acid Extract | 5.0 |
| Beta Glucan | 7.0 |
| Carbomer | 0.1 |
| Any one of Examples 1 to 4 | 0.1 |
| Caprylic/Capric Triglycerides | 8.0 |
| Squalane | 5.0 |
| Cetearyl Glucoside | 1.5 |
| Sorbitan stearate | 0.4 |
| Cetearyl Alcohol | 1.0 |
| Triethanolamine | 0.1 |

Preparation Example 2

Nourishing Cream

A nourishing cream was prepared by a conventional manner according to the composition shown in Table 8 below.

TABLE 8

| Components | Content(wt %) |
|---|---|
| Purified Water | Residual amount |
| Glycerin | 3.0 |
| Butylene glycol | 3.0 |
| Liquid Paraffin | 7.0 |
| Beta Glucan | 7.0 |
| Carbomer | 0.1 |
| Any one of Examples 1 to 4 | 3.0 |
| Caprylic/Capric Triglycerides | 3.0 |

TABLE 8-continued

| Components | Content(wt %) |
|---|---|
| Squalane | 5.0 |
| Cetearyl Glucoside | 1.5 |
| Sorbitan stearate | 0.4 |
| Polysorbate 60 | 1.2 |
| Triethanolamine | 0.1 |

Preparation Example 3

Massage Cream

A massage cream was prepared by a conventional manner according to the composition shown in Table 9 below.

TABLE 9

| Components | Content(wt %) |
|---|---|
| Purified Water | Residual amount |
| Glycerin | 8.0 |
| Butylene glycol | 4.0 |
| Liquid Paraffin | 45.0 |
| Beta Glucan | 7.0 |
| Carbomer | 0.1 |
| Any one of Examples 1 to 4 | 1.0 |
| Caprylic/Capric Triglycerides | 3.0 |
| Beeswax | 4.0 |
| Cetearyl Glucoside | 1.5 |
| Sorbitan Sesquioleate | 0.9 |
| Vaseline | 3.0 |
| Paraffin | 1.5 |

Preparation Example 4

Facial Pack

A facial pack was prepared by a conventional manner according to the composition shown in Table 10 below.

TABLE 10

| Components | Content(wt %) |
|---|---|
| Purified Water | Residual amount |
| Glycerin | 4.0 |
| Polyvinyl Alcohol | 15.0 |
| Hyaluronic acid Extract | 5.0 |
| Beta Glucan | 7.0 |
| Allantoin | 0.1 |
| Any one of Examples 1 to 4 | 0.5 |
| Nonylphenyl Ether | 0.4 |
| Polysorbate 60 | 1.2 |
| Ethanol | 6.0 |

Preparation Example 5

Ointment for External-Use Skin Preparation

An ointment was prepared by a conventional manner according to the composition shown in Table 11 below.

TABLE 11

| Components | Content (wt %) |
|---|---|
| Purified Water | Residual amount |
| Glycerin | 8.0 |

TABLE 11-continued

| Components | Content (wt %) |
|---|---|
| Butylene glycol | 4.0 |
| Liquid Paraffin | 15.0 |
| Beta Glucan | 7.0 |
| Carbomer | 0.1 |
| Any one of Examples 1 to 4 | 1.0 |
| Caprylic/Capric Triglycerides | 3.0 |
| Squalane | 1.0 |
| Cetearyl Glucoside | 1.5 |
| Sorbitan stearate | 0.4 |
| Cetearyl Alcohol | 1.0 |
| Beeswax | 4.0 |

The invention claimed is:

1. An external-use skin preparation composition comprising a natural ceramide, ceramide derivatives, and a *Hibisci cortex* extract, as active ingredients,
wherein the ceramide derivatives are 1,3-bis(N-(2-hydroxyethyl)-palmitoylamino)-2-hydroxypropane of the following Chemical Formula I and N-hexadecyl-N-palmitoyl)-1-aminopropane-2-sodium phosphate of the following Chemical Formula II:

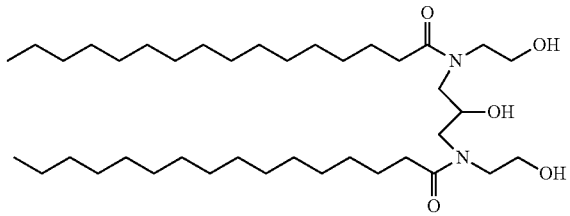

Chemical Formula I

Chemical Formula II

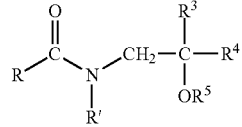

wherein, R is —$C_{15}H_{31}$, R' is —$C_{16}H_{33}$, $R^3$ is —$CH_3$, $R^4$ is hydrogen, and $R^5$ is

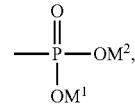

wherein $M^1$ and $M^2$ are each independently Na or hydrogen, wherein at least one of $M^1$ and $M^2$ is Na,
wherein the *Hibisci cortex* extract is prepared using water or an organic solvent as an extraction solvent,
wherein the natural ceramide is contained in an amount of 0.001 to 10% by weight, the ceramide derivatives are contained in an amount of 0.001 to 20% by weight, and the *Hibisci cortex* extract is contained in an amount of 0.001 to 20% by weight based on the total weight of the composition.

2. The external-use skin preparation composition of claim 1, wherein the natural ceramide, the ceramide derivatives, and the *Hibisci cortex* extract are mixed in a weight ratio of 1 to 300:1 to 500:1 to 500.

3. The external-use skin preparation composition of claim 1, wherein 1,3-bis(N-(2-hydroxyethyl)-palmitoylamino)-2- hydroxypropane and (N-hexadecyl-N-palmitoyl)-1-aminopropane-2-sodium phosphate are mixed in a weight ratio of 1 to 10:1 to 10.

4. The external-use skin preparation composition of claim 1, wherein the composition is a pharmaceutical composition further containing a dermatologically acceptable carrier or excipient.

5. The external-use skin preparation composition of claim 1, wherein the composition is a cosmetic composition further containing a cosmetically acceptable carrier or excipient.

6. A method selected from the following (a)-(c):
(a) improving skin moisturization of a subject;
(b) reducing skin wrinkles of a subject; or
(c) improving skin elasticity,
said method comprising administering the external-use skin preparation composition of claim 1 to target skin area of the subject.

* * * * *